United States Patent
Wright (12) 
(10) Patent No.: US 6,682,757 B1
(45) Date of Patent: Jan. 27, 2004

(54) TITRATABLE DOSAGE TRANSDERMAL DELIVERY SYSTEM

(75) Inventor: Curtis Wright, Norwalk, CT (US)

(73) Assignee: Euro-Celtique, S.A., Luxembourg (LU)

( * ) Notice: Subject to any disclaimer, the term of this patent is extended or adjusted under 35 U.S.C. 154(b) by 4 days.

(21) Appl. No.: 09/714,604

(22) Filed: Nov. 16, 2000

(51) Int. Cl.$^7$ .......................... A61L 15/16; A61F 13/00; A61F 15/00
(52) U.S. Cl. ................... 424/448; 424/449; 424/435; 424/434; 602/58
(58) Field of Search .................. 424/448, 449, 424/435, 434; 602/58

(56) References Cited

U.S. PATENT DOCUMENTS

| | | | |
|---|---|---|---|
| 4,573,996 A | 3/1986 | Kwiatek et al. | |
| 4,597,961 A | 7/1986 | Etscorn | |
| 4,666,441 A | 5/1987 | Audriola et al. | |
| 4,781,924 A | 11/1988 | Lee et al. | |
| 4,788,064 A | 11/1988 | Patel et al. | |
| 4,806,341 A | 2/1989 | Chien | |
| 4,837,027 A | 6/1989 | Lee et al. | |
| 4,839,174 A | 6/1989 | Baker et al. | |
| 4,840,796 A | 6/1989 | Sweet et al. | |
| 4,906,169 A | 3/1990 | Chien et al. | |
| 4,908,213 A | 3/1990 | Govil et al. | |
| 4,915,950 A * | 4/1990 | Miranda et al. | 424/447 |
| 4,943,435 A | 7/1990 | Baker et al. | |
| 5,023,084 A | 6/1991 | Chien et al. | |
| 5,066,494 A | 11/1991 | Becher | |
| 5,120,546 A | 6/1992 | Hansen et al. | |
| 5,163,899 A | 11/1992 | Sibalis | |
| 5,240,711 A | 8/1993 | Hille et al. | |
| 5,438,067 A * | 8/1995 | Jalonen et al. | 424/447 |
| 5,560,922 A | 10/1996 | Chien et al. | |
| 5,616,337 A * | 4/1997 | Kasianovitz et al. | 424/414 |
| 5,676,373 A | 10/1997 | Sakai et al. | |
| 5,676,969 A | 10/1997 | Wick et al. | |
| 5,686,112 A * | 11/1997 | Liedtke | 424/444 |
| 5,736,154 A | 4/1998 | Fuisz | |

(List continued on next page.)

FOREIGN PATENT DOCUMENTS

| | | |
|---|---|---|
| DE | 199 00 645 A1 | 7/2000 |
| EP | 0 298 297 A1 | 11/1991 |
| EP | 0 559 411 A1 | 9/1992 |

OTHER PUBLICATIONS

Edinboro et al., 1997, "Fatal fentanyl intoxication following excessive transdermal application", J. Forensic Sci. Jul;42(4):741–3.

(List continued on next page.)

*Primary Examiner*—Thurman K. Page
*Assistant Examiner*—Todd D Ware
(74) *Attorney, Agent, or Firm*—Pennie & Edmonds LLP (57) ABSTRACT

The present invention relates to a titratable dosage transdermal delivery system for systemic delivery of a therapeutic agent or drug. The system comprises a plurality of patch units that are connected along one or more borders. The plurality of patch units are divisible into units along the one or more borders having one or more lines of separation. Each patch unit is surrounded by a border. The therapeutic patch has at least a backing layer and a therapeutic agent comprising layer. The dosage of therapeutic agent delivered to a patient is proportional to the number of patch unit applied per treatment. The system enables systemic administration of a titratable dosage of therapeutic agent, adjustable by the patient under the direction of a physician, through the skin or mucosa. Moreover, the invention relates to a method of making the titratable dosage transdermal delivery system. Furthermore, the invention relates to a method of providing a titratable amount of therapeutic agent to a patient using the transdermal delivery system of the invention.

29 Claims, 4 Drawing Sheets

U.S. PATENT DOCUMENTS

| | | | |
|---|---|---|---|
| 5,879,701 | A | 3/1999 | Audett et al. |
| 5,902,603 | A | 5/1999 | Chen et al. |
| 5,919,477 | A | 7/1999 | Bevan et al. |
| 5,968,547 | A | 10/1999 | Reder |
| 6,007,837 | A | 12/1999 | Enscore et al. |
| 6,010,715 | A | 1/2000 | Wick et al. |
| 6,018,092 | A | 1/2000 | Dunshee |
| 6,054,120 | A * | 4/2000 | Burgoyne et al. ............. 424/59 |
| 6,143,320 | A | 11/2000 | Becher et al. |
| 6,221,384 | B1 * | 4/2001 | Pagedas ...................... 424/448 |
| 6,319,510 | B1 * | 11/2001 | Yates ......................... 424/402 |

OTHER PUBLICATIONS

Jeal W. & Benfield P., 1997, "Transdermal Fentanyl. A Review of its Pharmacological Properties and Therapeutic Efficacy in Pain Control", Drugs, 53(1):109–138.

Jordan WP Jr., 1997, "Allergy and topical irritation associated with transdermal testosterone administration: a comparison of scrotal and nonscrotal transdermal systems", Am J Contact Dermat. 8(2):108–13.

Jordan et al., 1998, "Comparison of the skin irritation potential of two testosterone transdermal systems: an investigational system and a marketed product", Clin Ther. 20(1):80–7.

Kemp et al., 1997, "Postmortem Distribution of Nicotine and Cotinine From a Case Involving the Simultaneous Administration of Multiple Nicotine Transdermal Systems", J. Anal. Toxicol. 21(4):310–313.

Korte et al., 1996, "Day–to–Day titration to initiate transdermal fentanyl in patients with cancer pain: short– and long–term experiences in a prospective study of 39 patients", J Pain Symptom Manage. 11(3):139–46.

Mahmood I., 1997, "Clinical pharmacokinetics and pharmacodynamics of selegiline. An update.", Clin Pharmacokinet. 33(2):91–102. Review.

Manitz et al., 1998, "On Mathematical Modeling of Dermal and Transdermal Drug Delivery", J. Pharm Sci. 87(7):873–879.

Meikle et al., 1996, "Pharmacokinetics and metabolism of a permeation–enhanced testosterone transdermal system in hypogonadal men: influence of application site– –a clinical research center study", J Clin Endocrinol Metab. 81(5):1832–40.

Meikle et al., 1992, "Enhanced transdermal delivery of testosterone across nonscrotal skin produces physiological concentrations of testosterone and its metabolites in hypogonadal men", J Clin Endocrinol Metab. 74(3):623–8.

Popli S et al., 1983, "Transdermal clonidine for hypertensive patients", Clin Ther. 5(6):624–8.

Riley S et al., 1992, "Comparison of two transdermal nitroglycerin systems: Transderm–Nitro and Nitro–Dur.", Clin Ther. 14(3):438–45.

Southam M.A., 1995, "Transdermal Fentanyl Therapy: System Design, Pharmacokinetics and Efficacy", Anti–cancer Drugs 6 Suppl. 3: 29–34.

Van Buskirk et al., 1997, "Scale–up Adhesive Transdermal Drug Delivery Systems", Pharm. Res. 14(7):848–852.

Wang et al., 2000, "Pharmacokinetics of transdermal testosterone gel in hypogonadal men:application of gel at one site versus four sites: a General Clinical Research Center Study", J Clin Endocrinol Metab. 85(3):964–9.

Woolf et al., 1996, "Self–poisoning among Adults Using Multiple Transdermal Nicotine Patches", J. Toxicol. Clin. Toxicol. 34(6):691–8.

Carroll, "Estrogen patch may be safer for heart than pill," Reuters Health, Apr. 2003.

* cited by examiner

TITRATABLE DOSAGE TRANSDERMAL DELIVERY SYSTEM

FIELD OF THE INVENTION

The present invention relates generally to a transdermal delivery system which is applied onto the skin or mucosa of a host, for systemic delivery of a therapeutic agent. More particularly, the invention is directed to a titratable dosage transdermal delivery system that comprises a plurality of patch units connected along one or more borders. The plurality of patch units are divisible into respective units along the one or more borders having one or more lines of separation. The dosage provided by the transdermal delivery system is proportional to the number of units applied by the user as determined by a physician. Each patch unit comprises at least a backing layer and a drug layer formulated with at least one therapeutic agent. The transdermal delivery system enables administration of a titratable dosage of therapeutic agent on a solid support to the skin or mucosa of a host. Furthermore, the invention is directed to a method of making the transdermal delivery system. Still further, the invention is directed to a method of providing a titratable amount of therapeutic agent to a host using the transdermal delivery system of the invention.

BACKGROUND OF THE INVENTION

One approach to sustained delivery of a therapeutic agent is the use of transdermal delivery system such as transdermal patches. Generally, transdermal patches contain a therapeutic agent and an adhesive which allows the transdermal device to adhere to the skin of a patient, allowing for the passage of the active agent from the device through the skin of the patient. Various advantages of using transdermal patches include constant rate of delivery of therapeutic agent, longer duration of action (the ability of the patch to adhere to the skin for 1, 3, 7 days or longer), non-invasive application, improved patient compliance, and the supply of therapeutic agent may be interrupted at any time by tearing off the system. The importance of this means of administration resides in the fact that therapeutic agent can be delivered to the bloodstream without traversing the gastrointestinal tract and avoiding a "first pass" through the hepatic system prior to reaching the target site. This would avoid any gastrointestinal incompatibility with the pharmaceuticals and unwanted destruction of the pharmaceuticals by metabolism in the gastrointestinal tract. Once the therapeutic agent has penetrated the skin layer, it is absorbed into the blood stream where it can exert a desired pharmacotherapeutic effect. These benefits may be obtained without requiring a professional to administer the therapeutic agent. Transdermal absorption minimizes inter- and intra-patient variations regarding such incompatibilities and metabolisms. By transdermal absorption, it is deemed possible to provide more constant pharmaceutical concentration in the body and to realize a greater pharmaceutical efficiency. It is possible, by proper transdermal absorption, to provide effective dosing of therapeutic agent.

Current pharmaceutical practice provides for transdermal system or transdermal patch that delivers therapeutics at fixed dosages. The rate of delivery of therapeutic agent from the patch to the skin or mucosa of a host, known as the flux rate, is constant and predetermined by the individual patch that is prescribed. The economics of manufacturing and government approval limit the availability of patches with different dosages. Presently, a pharmacist needs to stock multiple patches each containing various dosages of therapeutic agents. For example, a pharmacist needs to stock five different types of transdermal patch, each having dosage strengths such as 25, 50, 75, 100, 150 units per time (micrograms/hour). When a doctor prescribed a certain patch having a certain dosage strength to a patient, the patient purchases enough supply of transdermal patches having the fixed dosage of therapeutic agent. If the prescribed amount is too strong, the patient will have to purchase another supply of transdermal patches having a reduced dosage of therapeutic agent. If the prescribed amount is too weak, the patient will have to purchase another supply of transdermal patches having an increased dosage of therapeutic agent. In this current practice, patches that do not provide the optimum dosage for the patient are being wasted.

Thus, there remains a long felt, yet currently unmet need to provide a transdermal delivery system that can deliver titratable dosage of therapeutic agent. This titratable dosage transdermal delivery system has the advantage of minimizing wastage of transdermal patches that do not provide optimal dosage level of therapeutic agent. There is also a need for a transdermal system which allows fine control of dosage of therapeutic agent to be delivered to a patent. The transdermal delivery system of the present invention solves the problem by providing adjustable dosage of therapeutic agent from a single transdermal delivery system. This invention reduces the number of different types of transdermal patch having various dosage strengths that need to be stocked by a pharmacist. For example, the pharmacist mentioned above would only need to stock two types of transdermal delivery system of the present invention. One type has a dosage of 25 units per patch and the second type has a dosage of 75 units per patch unit. From these two types of patches, it is possible to deliver various dosage strengths such as 25, 50, 75, 100, 150 units. For example, in order to achieve a strength of 50 units, 2 patches of the 25 unit dosage per patch unit may be used. To achieve a strength of 100 units, 4 patches of the same type of patch may be used. To achieve a strength of 150 units, 2 patches of the 75 unit dosage per patch unit may be used. Instead of stocking five different kinds of patches containing different dosages, only two different kinds of patches need to be stocked.

SUMMARY OF THE INVENTION

The present invention is based upon the observation of the inventor that an optimal dosage of therapeutic agent may be delivered to the skin or mucosa of a host, by means of a titratable dosage transdermal delivery system. The present system addresses three shortcomings of the current technology. First, with the advent of transdermal patch, self-administration by a patient is generally involved. Patient compliance with application instructions takes on great importance. The present system provides an easy method of adjusting the dosage of therapeutic agent by the patient through the use of the system of the invention by following simple instructions from the physician. Second, the present system reduces the number of therapeutic patches with different dosages that need to be stocked by a pharmacist. Third, the present system reduces wastage of transdermal patches that have suboptimal dosage of therapeutic agent.

It is an object of this invention to provide a titratable dosage transdermal delivery system for the systemic delivery of one or more therapeutic agents to the skin or mucosa of a host.

The system comprises a plurality of patch units connected along one or more borders. Each patch unit comprises: a backing layer having a top surface and a bottom surface; a drug layer disposed on the top surface of the backing layer; and a means for adhering the patch unit onto the skin or mucosa of a host layer, where each patch unit is defined by one or more lines of separation on the border.

In one embodiment, the system comprises a plurality of patch units connected along one or more borders. Each patch unit comprises: (a) a backing layer having a top surface and a bottom surface; (b) a drug layer with matrix layer disposed on the top surface of the backing layer; and (c) an adhesive layer disposed on the drug layer with matrix layer, wherein each patch unit is defined by one or more lines of separation on the border.

In one embodiment, the system comprises a plurality of patch units connected along one or more borders. Each patch unit comprises: (a) a backing layer having a top surface and a bottom surface; (b) a drug layer with matrix layer disposed on the top surface of the backing layer; (c) an adhesive layer disposed on the drug layer with matrix layer; and (d) a cover layer disposed on the adhesive layer, wherein each patch unit is defined by one or more lines of separation on the border.

In another embodiment, the transdermal delivery system comprises a plurality of patch units connected along one or more borders. Each patch unit comprises: a backing layer having a top surface and a bottom surface; a drug and adhesive layer disposed on the top surface of the backing layer; and a cover layer disposed on the adhesive layer, wherein each patch unit is defined by one or more lines of separation on the border.

Moreover, it is an object of the present invention to provide a transdermal delivery system which comprises a plurality of patch units connected along one or more borders. Each patch unit comprises: a backing layer having a top surface and a bottom surface; a drug and adhesive layer disposed on the top surface of the backing layer; a release limiting layer disposed on the drug and adhesive layer; a second drug and adhesive layer disposed on the release limiting layer; and a cover layer disposed on the release limiting layer, wherein each patch unit is defined by one or more lines of separation on the border.

In addition, it is an object of the present invention to provide a method of making the transdermal delivery system which delivers a titratable dosage of drugs to a patient. The method comprises forming a backing layer with top and bottom surfaces, which backing layer is divided into more than one unit at one or more lines of separation. A drug-in-matrix layer is disposed on the top surface of each unit of the backing layer, leaving a border on all sides of the backing layer. An adhesive layer is disposed on the drug-in-matrix layer and the border of the backing layer. A cover layer is then disposed on top of the adhesive layer.

Still further, in one embodiment, the method comprises forming a plurality of reservoir compartments within an enclosure defined by the raised wall directly on a backing layer. Each reservoir compartment is surrounded by a border having a surface. One or more lines of separation are formed on the border dividing the plurality of the reservoir compartments into separate units. A drug layer is disposed into each of the reservoir compartments. An adhesive layer is then disposed on top of the drug layer and on the surface of the border. A cover layer is then disposed on the adhesive layer which covers the surface of the border and the adhesive layer.

Furthermore, it is an object of the present invention to provide a method of making the transdermal delivery system which delivers a titratable dosage of drugs to a patient. The method comprises forming a backing layer with top and bottom surfaces, which backing layer is divided into more than one units at one or more lines of separation. A drug-in-adhesive layer is disposed on the top surface of each unit of the backing layer, leaving a border on all sides of the backing layer. A cover layer is disposed on top of the adhesive layer.

Moreover, in one embodiment, the method comprises the steps of forming a backing layer with top and bottom surfaces, which backing layer is divided into more than one units at one or more lines of separation. A drug-in-adhesive layer is disposed on the top surface of each unit of the backing layer, leaving a border on all sides of the backing layer. A semi-permeable membrane is disposed on the backing film so as to hold the drug-in-adhesive within the border. A second drug-in-adhesive layer is disposed on the semi-permeable membrane. The border is covered with an adhesive. A cover layer is disposed on the drug-in-adhesive layer.

Finally, it is an object of the present invention to provide a method of delivering a therapeutic agent through the skin or mucosa of a patient. The method comprises providing a transdermal delivery system; separating a prescribed number of units of patches from the transdermal delivery system along at least one line of separation; and removing the cover layer exposing the adhesive layer and applying it on the skin or mucosa.

BRIEF DESCRIPTION OF THE DRAWINGS

The various advantages and novel features of this invention will be more apparent from a reading of the Detailed Description of the Present Invention in conjunction with the accompanying drawings in which like reference numerals refer to like parts.

DETAILED DESCRIPTION OF THE INVENTION

TRANSDERMAL DELIVERY SYSTEM OF THE INVENTION

Figure 1:
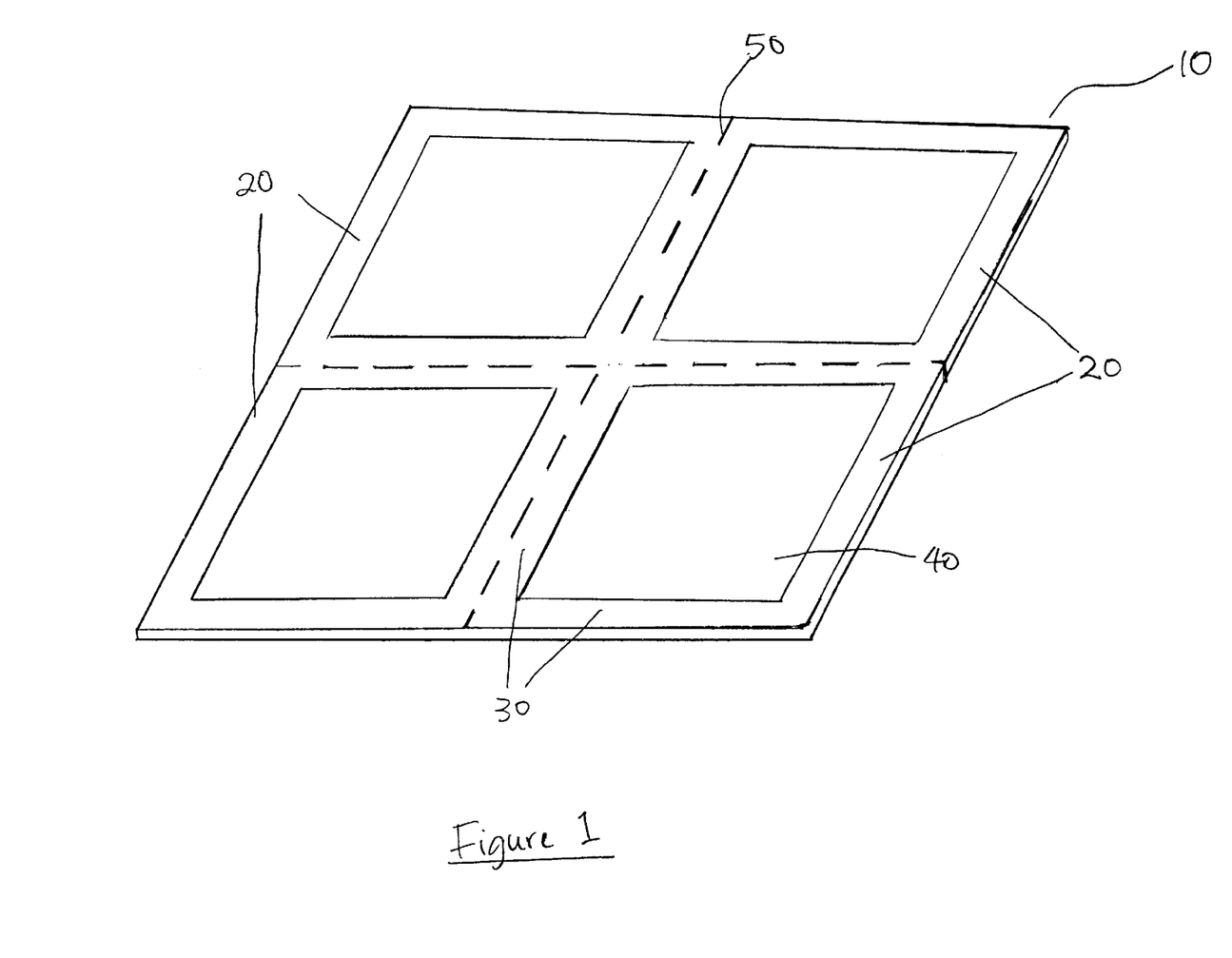
FIG. 1 illustrates a schematic diagram showing an embodiment of the transdermal delivery system of the invention.

In general, this invention is directed to a divisible transdermal delivery system which can deliver a titratable dosage of therapeutic agent to the skin or mucosa of a patient. The system of the present invention comprises a plurality of patch units joined together along one or more borders. In other words, the system comprises divisible units of therapeutic patch, thus delivering a controlled amount of therapeutic agent proportional to the number of patch units as desired. As illustrated in FIG. 1, the titratable transdermal delivery system 10 comprises a plurality of units. In this embodiment, there are four (4) units 20 in the system 10 arranged in 2 columns with 2 rows (i.e. 2×2 format). Each unit 20 comprises four borders 30 surrounding a therapeutic delivery zone 40. The plurality of therapeutic patches are divisible along the border. The border may be perforated to form a line of separation which facilitates division of the therapeutic patches into one or more units comprising one or more doses of therapeutic agent. In this embodiment, each unit 20 has two lines of separation 50.

Figure 2:
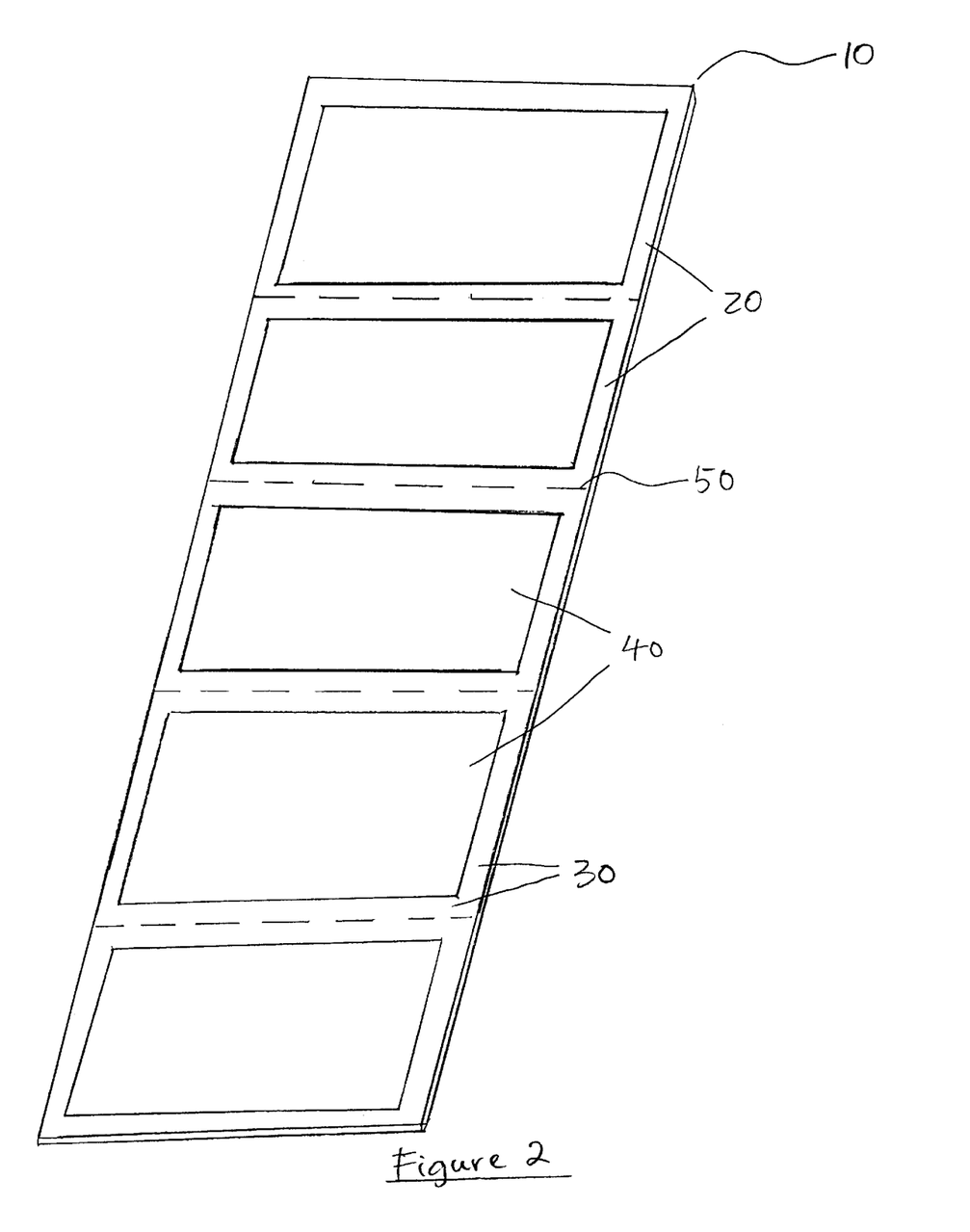
FIG. 2 illustrates a schematic diagram showing an embodiment of the transdermal delivery system of the invention.

In another embodiment as illustrated in FIG. 2, the titratable transdermal delivery system 10 comprises a plurality of therapeutic patch units arranged in a single row. Here, there are five (5) units 20 in the system 10. Each unit 20 comprises four borders 30 surrounding a therapeutic delivery zone 40. Similar to the embodiment in FIG. 1, the plurality of therapeutic patches are divisible along the border. In this embodiment, the two (2) units 20 at the ends of the transdermal delivery system 10 have one line of separation 50 whereas the three (3) units at the middle of the transdermal delivery system have two lines of separation.

A patch suitable for use with the invention should contain at least: (1) a backing layer and (2) a therapeutic agent comprising layer. Each patch unit is surrounded by a border which is free of therapeutic agents. The patch may comprise an adhesive means for securing to the surface of the skin or mucosa. In a preferred embodiment, a cover layer is also present to protect the therapeutic agent comprising layer. In another preferred embodiment, the cover layer comprises a hermetic peelable seal which may be formed by heat sealing or an adhesive. In another preferred embodiment, the cover layer has a notch which provides for easy separation of the cover layer from the patch.

Preferred patches that are suitable for use in this invention include, for example, (1) the matrix type patch; (2) the reservoir type patch; (3) the monolithic drug-in-adhesive type patch; and (4) the multi-laminate drug-in-adhesive type patch (Ghosh, T. K.; Pfister, W. R.; Yum, S. I. *Transdermal and Topical Drug Delivery Systems*, Interpharm Press, Inc. p. 249–297). These patches are well known in the art. Other patches may be useful for the present invention as determined by one of skill in the art.

For practice of the invention, the matrix type patches are the most preferred.

MATRIX TYPE TRANSDERMAL SYSTEM

Figure 3A:
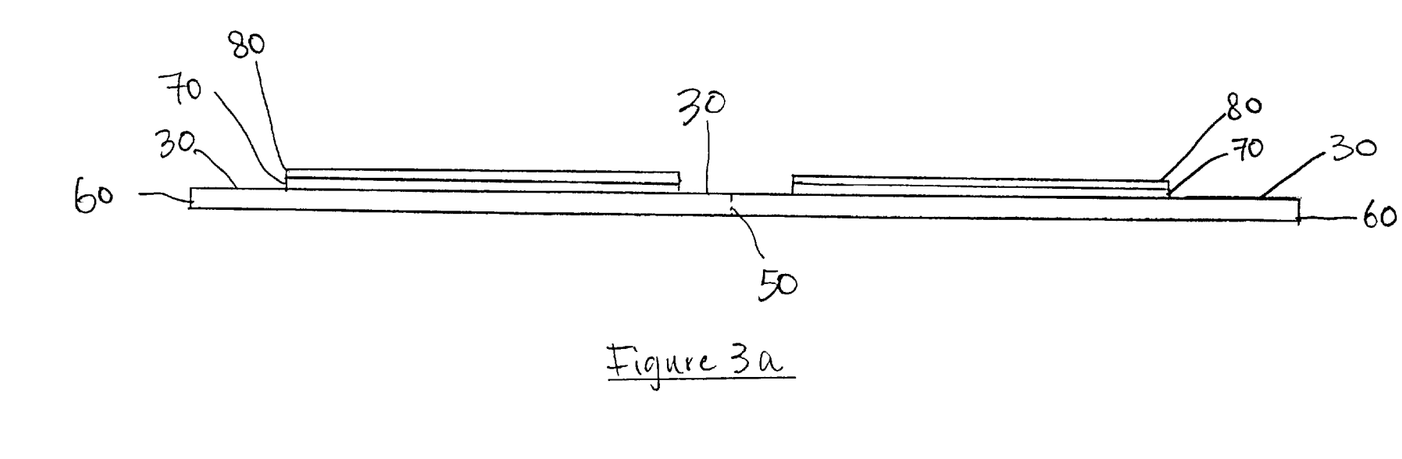
FIG. 3a illustrates a schematic diagram showing a cross-section of a matrix type transdermal delivery system of the invention.

FIG. 3a illustrates an embodiment of the system of the invention which utilizes a matrix patch. The matrix patch comprises a backing layer 60 which comprises two opposing surfaces. One of the surface is in contact with a drug with matrix layer 70, which is a matrix layer containing a therapeutic agent, and an adhesive layer 80. The drug with matrix layer 70 does not cover the entire area of the patch unit but are confined at the drug delivery zone 40 as shown in FIGS. 1 and 2, leaving a border 30 surrounding the drug delivery zone 40. A line of separation 50 divides the borders 30 of adjacent patch units 20. The line of separation facilitates the division of the system into separate units. The line of separation may be formed by perforations or weaknesses created in the backing layer.

In a preferred embodiment, a release liner (not shown) is disposed on the adhesive layer 80 or the drug with matrix layer 70. In some cases, it may be necessary to include an impermeable layer (not shown) on the surface of the backing layer 60 that is in contact with the drug with matrix layer 70 to minimize drug migration into the backing film (e.g., U.S. Pat. No. 4,336,243). The matrix containing the therapeutic agent is held against the skin by the adhesive layer 80. Adhesives may also be present on the surface of the borders 30 to provide further adhesion for the patch to the skin.

The backing layer may be formed of woven or braided fibers or wires, membranes, porous or fibrous scaffolds made of a polymer. The polymer(s) useful for forming the therapeutic patch should be ones that are biocompatible and avoid irritation to the skin or mucosa. The backing layer can be made of a pharmaceutically acceptable material which is impermeable to the therapeutic agent used. The backing layer preferably serves as a protective cover for the therapeutic agent and may also provide a support function. Examples of materials suitable for making the backing layer are synthetic polymers like films of high and low density polyethylene, polypropylene, polyvinylchloride, polyurethane, polyesters such as poly(ethylene phthalate), metal foils, metal f&oil laminates of suitable polymer films, textile fabrics. Other examples for backing materials are from natural materials like cotton, wool, etc. Preferably, the materials used for the backing layer are laminates of such polymer films with a metal foil such as aluminum foil. One preferred type of backing material is nonwoven urethane material, such as described in, for example, U.S. Pat. No. 5,230,701 to Meyer et al. More preferably the backing films are occlusive and comprised of a polyolefin oil. Occlusive backing films, such as synthetic polyesters, result in hydration of the outer layers of the stratum corneum while non-occlusive backings allow the area to breath (i.e., promote water vapor transmission from the skin surface). The backing layer can be any appropriate thickness which will provide the desired protective and support functions. A suitable thickness will be from about 10 to about 200 microns. Desirable materials and thickness will be apparent to the skilled artisan.

Generally, the matrix layer is formed from biologically acceptable polymers capable of forming thin walls or coatings through which pharmaceuticals can pass at a controlled rate. Examples of suitable matrix materials include but are not limited to lipophilic polymers, such as polydimethylsiloxane, and hydrophilic polymers like polyvinylpyrrolidone, polyvinyl alcohol, hydrogels based on gelatin, or polyvinylpyrrolidone/polyethylene oxide mixtures. A non-limiting list of exemplary materials for inclusion in the polymer matrix includes polyethylene, polypropylene, ethylene/propylene copolymers, ethylene/ethylacrylate copolymers, ethylenevinyl acetate copolymers, silicones, rubber, rubber-like synthetic homo-, co- or block polymers, polyacrylic esters and the copolymers thereof, polyurethanes, polyisobutylene, chlorinated polyethylene, polyvinylchloride, vinyl chloride-vinyl acetate copolymer, polymethacrylate polymer (hydrogel), polyvinylidene chloride, poly(ethylene terephthalate), ethylene-vinyl alcohol copolymer, ethylene-vinyloxyethanol copolymer, silicones including silicone copolymers such as polysiloxane-polymethacrylate copolymers, cellulose polymers (e.g., ethyl cellulose, and cellulose esters), polycarbonates, polytetrafluoroethylene and mixtures thereof.

Preferred materials for inclusion in the matrix layer can be any silicone elastomers of the general polydimethylsiloxane structures, e.g., silicone polymers. Preferred are cross-linked silicone polymers that are pharmaceutically acceptable. Other preferred materials for inclusion in the polymer matrix layer include: silicone polymers that are cross-linkable copolymers having dimethyl and/or dimethylvinyl siloxane units which can be crosslinked using a suitable peroxide catalyst. Also preferred are those polymers consisting of block copolymers based on styrene and 1,3-dienes (particularly linear styrene-isoprene-block copolymers of styrene-butadiene-block copolymers), polyisobutylenes, polymers based on acrylate and/or methacrylate.

The polymer matrix layer may optionally include a pharmaceutically acceptable crosslinking agent. Suitable crosslinking agents include, e.g., tetrapropoxy silane.

An adhesive layer may be used to affix the transdermal patch to the skin of the patient for a desired period of administration, e.g., about 5 to about 8 days. If the adhesive layer of the transdermal patch fails to provide adhesion for the desired period of time, it is possible to maintain contact between the transdermal patch with the skin by, for instance, affixing the transdermal patch to the skin of the patient with an adhesive tape, e.g, surgical tape. It is not critical for purposes of the present invention whether adhesion of the transdermal patch to the skin of the patient is achieved solely by the adhesive layer of the transdermal patch or in connection with a peripheral adhesive source, such as surgical tape, provided that the transdermal patch is adhered to the patient's skin for the requisite administration period.

The adhesive layer is preferably an active ingredient permeable adhesive layer that joins the device to the skin or mucosa of the host. It is also preferably dermatologically acceptable. Each active ingredient permeable adhesive layer is preferably a pressure-sensitive adhesive. Any of the well-known, dermatologically acceptable, pressure-sensitive adhesives which permit drug migration therethrough can be used in the present invention.

Some suitable permeable adhesives include acrylic or methacrylic resins such as polymers of alcohol esters of acrylic or methacrylic acids and alcohols such as n-butanol, isopentanol, 2-methylbutanol, 1-methylbutanol, 1-methylpentanol, 2-methylpentanol, 3-methylpentanol, 2-ethyl-butanol, isooctanol, n-decanol, or n-dodecanol, alone or copolymerized with ethylenically unsaturated monomers such as acrylic acid, methacrylic acid, acrylamide, methacrylamides, N-alkoxymethyl acrylamides, N-alkoxymethyl methacrylamides, N-t-butylacrylamide, itaconic acid, vinyl acetate, N-branched alkyl maleamic acids wherein the alkyl group has 10–24 carbon atoms, glycol diacrylates, or mixtures of these monomers; polyurethane elastomers; vinyl polymers such as polyvinyl alcohol, polyvinyl ethers, polyvinyl pyrrolidone, and polyvinyl acetate; urea formaldehyde resins; phenol formaldehyde resins, resorcinol formaldehyde resins; cellulose derivatives such as ethylcellulose, ethylcellulose, nitrocellulose, cellulose acetate butyrate and carboxymethylcellulose; and natural gums such as guar, acacia, pectina, starch, destria, gelatin, casein, etc. Other suitable pressure-sensitive adhesives include polyisobutylene pressure-sensitive adhesives, rubber pressure-sensitive adhesives and silicone pressure-sensitive adhesives. he adhesives may also be compounded with tackifiers and stabilizers as is well-known in the art. Any of the well known dermatologically acceptable hypoallergenic pressure-sensitive adhesives can be used in practicing this invention. Exemplary adhesives include acrylic or methacrylic resins such as polymers of esters of acrylic or methacrylic acid with alcohols such as n-butanol, n-pentanol, isopentanol, 2-methyl butanol, 1-methyl butanol, 1-methyl penanol, 2-methyl penanol, 3-methyl pentanol, -ethyl butanol, isooctanol, n-decanol, or n-dodecanol, alone or copolymerized with ethylenically unsaturated monomers such as acrylic acid, methacrylic acid, acrylamide, methacrylamide, N-alkoxymethyl acrylamides, N-alkoxymethyl methacrylamides, N-tert.butylacrylamide, itaconic acid, vinylacetate, N-branched alkyl maleamic acids wherein the alkyl group has 10 to 24 carbon atoms, glycol diacrylates, or mixtures of these; natural or synthetic rubbers such as styrenebutadiene, butylether, neoprene, polyisobutylene, polybutadiene, and polyisoprene; polyvinylacetate; ureaformaldehyde resins; phenolformaldehyde resins; resorcinol formaldehyde resins, cellulose derivatives such as ethyl cellulose, methyl cellulose, nitrocellulose, cellulose acetatebutyrate, and carboxymethyl cellulose; and natural gums such as guar, acacia, pectins, starch, dextrin, albumin, gelatin, casein, etc. The adhesives may be compounded with tackifiers and stabilizers as is well known in the art.

Adhesives that are preferred for their active agent permeability include acrylic copolymer adhesives such as Avery Chemical Company's AS-351 HSX, preferably at a coating weight of between 25 and 35 g/m.sup.2. This pressure-sensitive adhesive is a cross-linkable polymer which provides a permanently tacky film having a total solids content of about 52%, Brookfield viscosity (LVT/Spindle No. 4/12 RPM @ 25.degree. C.) of from about 15,000 to 25,000 cps. at a weight per gallon of about 7.4 lbs. It can also be diluted with hexane or toluene to a desired solids and/or viscosity range, particularly for use in conventional coating equipment.

In preferred embodiments, the transdermal patch includes a removable protective cover layer. The protective cover layer is removed prior to application, and consists of the materials used for the backing layer described above provided that they are rendered removable, for example, by a silicone treatment. Other removable protective cover layers, for example, are polyletra-fluoroethylene, treated paper, allophane, polyvinyl chloride, and the like. Generally, the removable protective layer is in contact with the adhesive layer and provides a convenient means of maintaining the integrity of the adhesive layer until the desired time of application.

In another preferred embodiment, the transdermal delivery system comprises a plurality of therapeutic patches which are stored in a resealable pouch.

RESERVOIR TYPE TRANSDERMAL SYSTEM

Figure 3B:
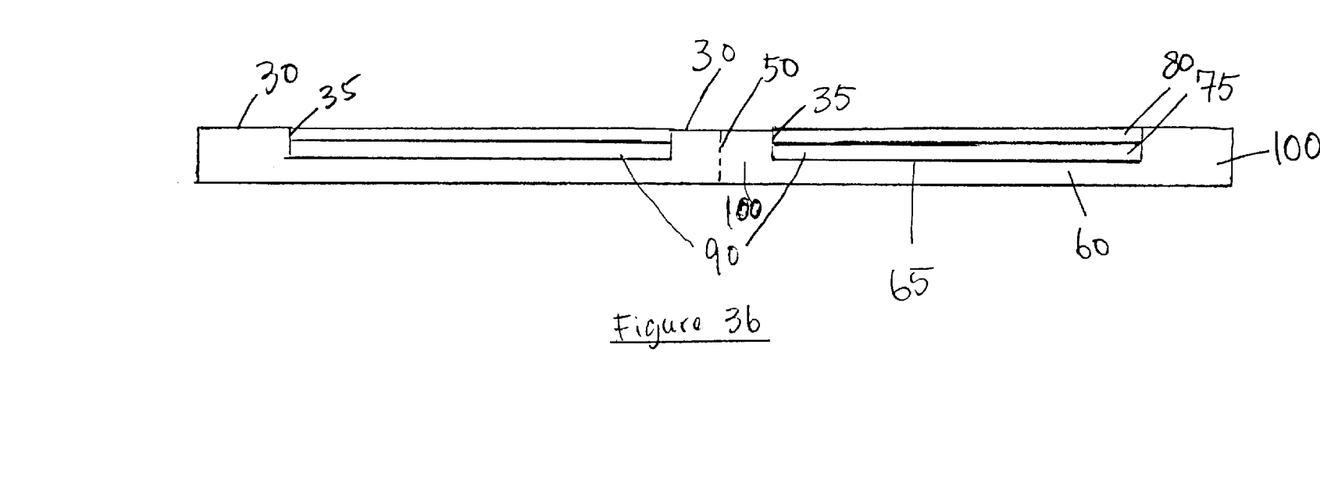
FIG. 3b illustrates a schematic diagram showing a cross-section of a reservoir type transdermal delivery system of the invention.

FIG. 3b illustrates an embodiment of the system of the present invention which uses a reservoir type patch. The reservoir type patch design is characterized by a backing layer 60 and a reservoir compartment 90 containing a drug layer 75 preferably, in the form of a solution or suspension, that is separated from the skin by a semipermeable membrane (not shown) (e.g., U.S. Pat. No. 4,615,699). The reservoir compartment 90 is a continuation of backing layer 60. The backing layer 60 is molded and formed having sidewalls 35 that defines the protected volume of the reservoir compartment 90. The amount of drug that may be placed within the reservoir compartment 90 is defined by the dimensions of the reservoir compartment 90 and the height of the sidewalls 35. The backing layer 60 has an upper surface 65, a side wall 35, defining a drug delivery zone 40 as shown in FIGS. 1 and 2, and a reservoir compartment 90 extending throughout the entire drug delivery zone 40. An adhesive layer 80 is disposed on top of the drug layer 75 and on the surface of the backing layer 65 which extends around the reservoir's boundaries, forming the border 30, so as to provide a seal with the skin and hold the reservoir adjacent to the skin or mucosa where a desirable number of unit patches of the transdermal system may be applied. At the border, a line of separation 50 extends throughout the raised walls 100 that are formed by the backing layer 60.

In one embodiment, the drug delivery zone 40 is rectangular. Alternatively, the drug delivery zone 40 may be a variety of shapes, such as, but not limited to, oval, circular, elliptical, triangular, rectangular, hexagonal. In a preferred embodiment, the drug delivery zone 40 has the same shape and therefore concentric to a patch unit of the transdermal system.

Other pharmaceutically acceptable compounds which may be included in the reservoir or matrix include: solvents, for example alcohols such as isopropanol; permeation enhancing agents such as those described infra; and viscosity agents, such as cellulose derivatives, natural or synthetic gums, such as guar gum, and the like.

Certain preferred transdermal delivery systems also include a softening agent in the reservoir or matrix. Suitable softening agents include higher alcohols such as dodecanol, undecanol, octanol, esters of carboxylic acids, wherein the alcohol component may also be a polyethoxylated alcohol, diesters of dicarboxylic acids, such as di-n-butyladiapate, and triglycerides particularly medium-chain triglycerides of the caprylic/capric acids or coconut oil, have proved to be particularly suitable. Further examples of suitable softeners are multivalent alcohols, for example, levulinic acid, cocprylic acids glycerol and 1,2-propanediol which can also be etherified by polyethylene glycols.

MONOLITHIC DRUG-IN-ADHESIVE TRANSDERMAL SYSTEM

Figure 3C:
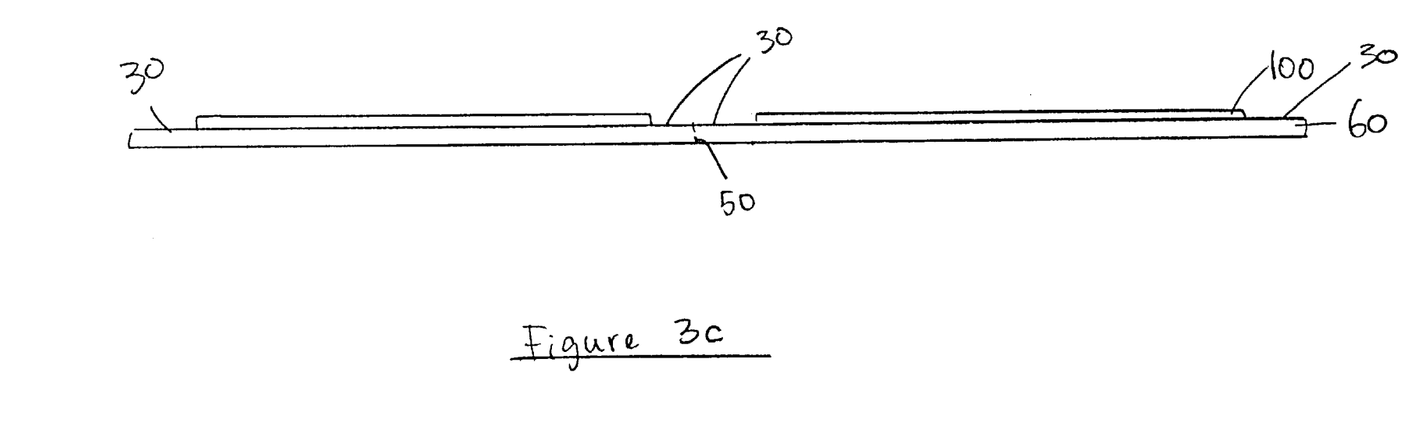
FIG. 3c illustrates a schematic diagram showing a cross-section of a monolithic drug-in-adhesive type transdermal delivery system of the invention.

FIG. 3c illustrates an embodiment of the system of the present invention that uses a monolithic drug-in-adhesive patch. The monolithic drug-in-adhesive patch design is characterized by the inclusion of the therapeutic agent formulation in the skin contacting adhesive layer forming the drug-in-adhesive layer 100, a backing layer 60 and preferably, a release liner (not shown). The adhesive releases the therapeutic agent and also adheres the patch to the skin. The drug-in-adhesive system does not require a separate adhesive layer and thus the patch thickness is minimized (e.g., U.S. Pat. No. 4,751,087). Therefore, drug-in-adhesive type patches are thin and comfortable. As illustrated in FIGS. 1 and 2, each unit of the transdermal system comprises one or more borders made of the backing layer surrounding a drug delivery zone 40. The drug-in-adhesive layer 100 does not cover the entire area of the unit of the patch but are confined at the drug delivery zone 40 as shown in FIGS. 1 and 2, leaving a border 30 surrounding the drug delivery zone 40. The border 30 is covered with an adhesive to further secure the unit of the therapeutic patch onto the skin. As in any patch designs, the plurality of therapeutic patches are divisible along the border. The border may be perforated to form a line of separation 50 which facilitates division of the therapeutic patches into one or more patch units comprising one or more doses of therapeutic agent or drug respectively.

MULTILAMINATE DRUG-IN-ADHESIVE TRANSDERMAL SYSTEM

Figure 3D:
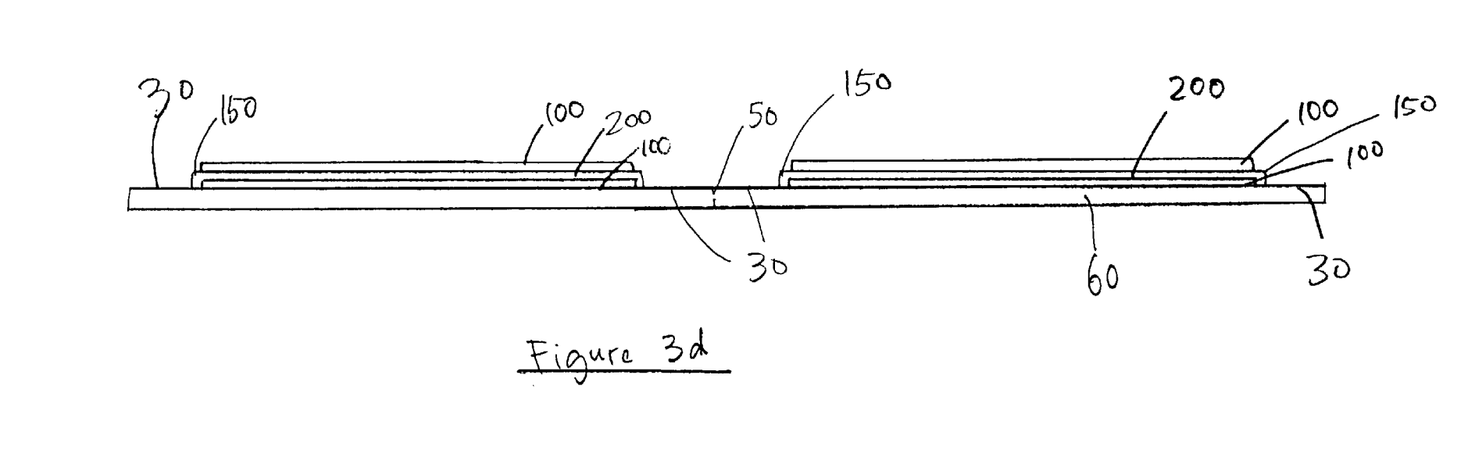
FIG. 3d illustrates a schematic diagram showing a cross-section of a multilaminate drug-in-adhesive type transdermal delivery system of the invention.

FIG. 3d illustrates an embodiment of the system of the present invention that utilizes a multi-laminate drug-in-adhesive patch. The multi-laminate drug-in-adhesive patch design further incorporates additional semi-permeable membrane 200 between two or more distinct drug-in-adhesive layers 100 under a single backing layer 60 (Peterson, T. A. and Dreyer, S. J. Proceed. *Intern. Symp. Control. Rel Bioact. Mater.* 21: 477–478). Each layer of the drug-in-adhesive layer 100 or the semi-permeable membrane 200 does not cover the entire area of the patch unit but are confined at the drug delivery zone as shown in FIGS. 1 and 2, leaving a border 30 surrounding the drug delivery zone. The edges 150 of each of the semi-permeable membrane 200 are secured to the backing film 60 so as to hold the drug-in-adhesive layer in place. The border 30 is covered with an adhesive to further secure the therapeutic patch unit onto the skin. As in any patch designs, the plurality of therapeutic patches are divisible along the border. The border may be perforated to form a line of separation 50 which facilitates division of the therapeutic patches into one or more units comprising one or more doses of therapeutic agent or drug respectively. In one embodiment, a release limiting layer may be used with any patch designs especially the reservoir or multi-laminate patch, including thin non-porous ethylene vinyl acetate films or thin microporous films of polyethylene employed in microlaminate solid state reservoir patches. Suitable release limiting layer include but are not limited to occlusive, opaque, or clear polyester films with a thin coating of pressure sensitive release liner (e.g., silicone-fluorsilicone, and perfluorcarbon based polymers). The release limiting layer materials of this invention, which may or may not be rate controlling as desired, are known in the art. The release limiting layers are commercially available and can be made by a multitude of different methods, as described in R. E. Kesting, Synthetic Polymer Membranes, McGraw Hill, Chapters 4 and 5, 1971; J. D. Ferry, Ultra-filtration Membranes, Chemical Review, Vol. 18, Page 373, 1934. In order to obtain the most advantageous results, the materials should be formed into structures with the desired morphology in accordance with methods known to those skilled in the art to achieve the desired release rate of drug. Additionally, the material must have the appropriate chemical resistance to the drug used and be non-toxic when used as an element of the patch of the invention. Materials useful in forming a rate controlling limiting layer used in this invention include, but are not limited to the following: Polycarbonates, i.e., linear polyesters of carbonic acids in which carbonate groups recur in the polymer chain, by phosgenation of a dihydroxy aromatic such as bisphenol A. Such material are sold under the trade designation Lexan by the General Electric Company. Polyvinylchlorides; one such material is sold under the trade designation Geon 121 by B.G. Goodrich Chemical Company. Polyamides such as polyhexamethylene adipamide and other such polyamides popularly known as "nylon". Modacrylic copolymers, such as that sold under the trade designation DYNEL are formed of polyvinylchloride (60 percent) and acrylonitrile (40 percent), styrene-acrylic acid copolymers, and the like. Polysulfones such as those of the type characterized by diphenylene sulfone groups in the linear chain thereof are useful. Such materials are available from Union Carbide Corporation under the trade designation P-1700. Halogenated polymers such as polyvinylidene fluoride sold under the trade designation Kynar by Pennsalt Chemical Corporation, polyvinylfluoride sold under the trade name Tedlar by E. I. DuPont de Nemours & Co., and the polyfluorohalocarbon sold under the trade name Aclar by Allied Chemical Corporation. Polychlorethers such as that sold under the trade name Penton by Hercules Incorporated, and other such thermoplastic polyethers. Acetal polymers such as the polyformaldehyde sold under the trade name Delrin by E. I. DuPont de Nemours & Co., and the like. Acrylic resins such as polyacrylonitrile polymethyl methacrylate, poly n-butyl methacrylate and the like. Other polymers such as polyurethanes, polyimides, polybenzimidazoles, polyvinyl acetate, aromatic and aliphatic, polyethers, cellulose esters, e.g., cellulose triacetate; cellulose; collodion (cellulose nitrate with 11% nitrogen); epoxy resins; olefins, e.g., polyethylene polypropylene; porous rubber; cross linked polyethylene oxide; cross-linked polyvinylpyrrolidone; cross-linked polyvinyl alcohol; polyelectrolyte structures formed of two ionically associated polymers of the type as set forth in U.S. Pat. Nos. 3,549,016 and 3,546,141; derivatives of polystyrene such as polysodium styrenesulfonate and polyvinylbenzyltrimethyl-ammonium chloride; polyhydroxyethylmethacrylate; polyisobutylvinyl ether, and the like, may also be utilized. A large number of copolymers which can be formed by reacting various proportions of monomers from the aforesaid said list of polymers are also useful for preparing rate controlling limiting layer utilized in the invention.

The rate controlling release limiting layer can have varying thickness depending upon the nature of the membrane, its porosity and the number of membranes used in combination. Typically, a thickness of from 20 to 200 microns is employed.

APPLICABLE THERAPEUTIC AGENTS

The applicable therapeutic agents which can be placed on the transdermal patch can be any therapeutic substances or drugs. The therapeutic agent can be of various physical states, e.g., molecular distribution, crystal forms or cluster forms. A therapeutic agent may be encapsulated by liposomes. Liposome comprising therapeutic agent useful in the present invention may be prepared in a number of ways known in the art. For example, microencapsulation techniques for the preparation of microcapsules having a wall or membrane of polymeric material are described in literature such as "Microencapsulation and Related Drug Processes" by P. D. Deasy, Marcel Dekker Inc. New York (1984).

In practicing this invention one can employ any systemically active drug hich may be absorbed by the body surface to which the transdermal patch is applied, onsistent with their known dosages and uses. Of course, the amount of drug necessary o obtain the desired therapeutic effect will vary depending on the particular drug used. uitable systemic drugs for administration by the claimed system include those useful in reating emesis and nausea as described in U.S. Pat. No. 4,031,894, e.g., preferably, copalamine. Other suitable systemic drugs are disclosed in U.S. Pat. No. 3,996, 934 and include, without limitation, anti-microbial agents such as penicillin, tetracycline, oxytetracycline, chlortetracycline, chloramphenicol, and sulfonamides; potent narcotics and analgesics such as fentanyl and etorphine; and local anaesthetics such as buprenorphine, penzocaine, morphine and morphine derivatives, lidocaine, prilocaine, mepivacaine or non-steroidal antirheumatics/anti-inflammatories such as indometnacin, diclofenac or etopenamate; sedatives such as pentabarbital sodium, phenobarbital, secobarbital sodium, codeine, (a-bromoisovaleryl) urea, carbromal, and sodium phenobarbital, psychis energizers such a 3-(2-aminopropyl) indole acetate and 3-(2-aminobutyl) indole acetate; tranquilizers such as reserpine, chlorpromazine hydrochloride, and thiopropazate hydrochloride; hormones such as adrenocorticosteroids, for example 6-α-methylprednisolone; androgenic steroids, for example, methyltestosterone, and fluoxymesterone; estrogenic steroids, for example estrone, 17-β-estradiol and ethinyl estradiol; progesterone, and norethindrone; and thyroxine; antipyretics such as aspirin, salicylamide, and sodium salicylate; morphine and other narcotic analgesics; anti-diabetics, e.g., insulin; cardiovascular agents, e.g. nitroglycerin, and cardiac glycosides such as digitoxin, digoxin, ouabain; anti-spasmodics such as atropine, methscopolamine bromide, methscopolamine bromide with phenobarbital; anti-malarials such as the 4-aminoquinolines, 9-amino-quinolines, and pyrimethamine; and nutritional agents such as vitamins, essential amino acids, and essential fats.

Additionally, in practicing this invention one can employ a wide variety of topically active drugs consistent with their known dosages and uses. Suitable drugs include, without limitation: antiperspirants, e.g., aluminum chloride; deodorants, e.g., hexachloraphene, methylbenzethonium chloride; astringents, e.g., tannic acid; irritants, e.g., methyl salicylate, camphor, cantharid; keratolytics, e.g., benzoic acid, salicylic acid, resorcinol, iodochlorhydroxyquin; antifungal agents, such as tolnaftate, griseofulvin, nystatin and amphotericin; anti-inflammatory agents, such as corticosteroids, e.g., hydrocortisone, hydrocortisone acetate, prednisolone, methylprednisolone, triamoinolone acetonide, fludrocortisone, flurandrenolone, flumethasone, dexamethasone sodium phosphate, bethamethasone, desamethasone sodium phosphate, bethamethasone valerate, fluocinolone acetonide; fluorometholone; and pramoxine HCl; anti-neoplastic agents, e.g. methotrexate, and antibacterial agents, such a bacitracin, neomycin, erythromycin, tetracycline HCl, chlortetracycline HCl, chloramphenicol, oxytetracycline, polymyxin B, nitrofuraxone, mafenide (alpha -amino-p-toluenesulfonamide), hexachlorophene, benzalkonium chloride, cetalkonium chloride, methylbenzethonium chloride, and neomycin sulfate.

It will be appreciated, with regard to the aforesaid list of drugs the characterization of the drug as either "systemically or topically" active is for classification purposes, a given drug can be both systemically and topically active depending upon its manner of use.

Drugs employed to assist in treating problems associated with cardiac dilation may be a suitable therapeutic agent for use in the present invention. For example, digoxin angiotensin-converting enzyme, ACE inhibitors, such as captopril and enalopril, may be used.

Other suitable drugs include the coronary vasodilators described in U.S. Pat. No. 3,742,951 such as compounds having nitrate moiety. Some suitable coronary vasodilators include organic and inorganic nitrates such as amyl nitrate, nitroglycerin glyceryl trinitrate), sodium nitrate, erythrityl tetranitrate, pentaerythritol tetranitrate, isosorbide dinitrate, mannitol hexanitrate, trolnitrate phosphate (triethanolamine biphosphate), and the like. Nitroglycerine is a preferred coronary vasodilator. Also suitable are the beta adrenegic blocking drugs such as propanolol.

When practicing the invention, antifungal agents such as ciclopirox, chloroxylenol, triacetin, sulconazole, nystatin, undecylenic acid, tolnaftate, miconizole, clotrimazole, oxiconazole, griseofulvin, econazole, ketoconozole, and amphotericin B may be incorporated. Antibiotic agents such as mupirocin, erythromycin, clindamycin, gentamicin, polymyxin, bacitracin, silver sulfadiazine, and the like may also be used. Antiseptic agents such as iodine, Povidine-iodine, benzalkonium chloride, benzoic acid, chlorhexidine, nitrofurazone, benzoyl peroxide, hydrogen peroxide, hexachlorophene, phenol, resorcinol, and cetylpyridinium chloride likewise could be incorporated into the topical drug formulation or the patch. Furthermore, anti-inflammatories such as hydrocortisone, prednisone, triamcilolone, betamethasone, dexamethasone, and the like may be incorporated.

In addition to the aforementioned drugs, simple pharmacologically acceptable derivatives of the drugs, such as ethers, esters, amides, acetals, salts, etc., or formulations of these drugs, having the desired polymeric permeability or transport or transport properties can be prepared and used in practicing the invention. Drugs mentioned above can be used along or in combination with others and each other.

The above drugs and other drugs can be present in the therapeutic patch of the invention alone or in combination form with pharmaceutical carriers. The pharmaceutical carriers acceptable for the purpose of this invention are the known in the art carriers that do not adversely affect the drug, the host, or the material comprising the transdermal delivery system. Suitable pharmaceutical carriers include sterile water; saline, dextrose; dextrose in water or saline, condensation products of castor oil and ethylene oxide combining about 30 to 35 moles of ethylene oxide per mole of castor oil; liquid glyceryl triester of a lower molecular weight fatty acid; lower alkanols, oils such as corn oil, peanut oil, sesame oil and the like, hydrocarbons such as mineral oils and silicones, with emulsifiers such as mono- or di-glyceride of a fatty acid, or a phosphatide, e.g., lecithin, and the like; glycols; polyalkylene glycols; aqueous media in the presence of a suspending agent, for example, sodium carboxymethylcellulose; sodium alginate; polyvinyl pyrrolidone; and the like, alone, or with suitable dispersing agents such as lecithin; polyoxyethylene stearate; and the like. The carrier may also contain adjuvants such as preserving, stabilizing, wetting, emulsifying agents, and the like.

A great number of systemically active drugs have been found to be suitable for administration via the transdermal route. Certain pharmaceuticals are absorbed to a degree through the skin. This is referred to as transdermal pharmaceutical absorption. It has been found that the transdermal absorption rates of certain pharmaceuticals can be increased by use of absorption promoting compounds (also referred to as skin permeation enhances) with the pharmaceutical to be absorbed.

Penetration enhancers can be included in the drug formulation or patch, to optimize delivery into and through the skin. Ghosh, T. K. et al. 1993, *Pharm. Tech.* 17(3):72–98; Ghosh, T. K. et al. 1993, *Pharm. Tech.* 17(4): 62–89; Ghosh, T. K. et al., 1993, *Pharm. Tech.* 17(5):68–76. Permeation enhancing agents are compounds which promote penetration and/or absorption of the therapeutic agent into the blood stream of the patient. The penetration enhancer should be pharmacologically inert, non-toxic, and non-allergenic, have rapid and reversible onset of action, and be compatible with the drug formulation (Pfister et al., 1990, *Pharm. Tech.* 14(9):132–140, incorporated herein by reference). Penetration enhancers suitable for the purpose of the invention do not adversely affect the host, the drug, or alter or adversely affect the materials forming the transdermal delivery system. The penetration enhances can be used alone or they can be admixed with acceptable carriers and the like.

Useful penetration enhancers include but are not limited to ethyl alcohol, isopropyl alcohol, or octolyphenylpolyethylene glycol. More preferred penetration enhancers include oleic acid, polyethylene glycol 400, propylene glycol, N-decylmethylsulfoxide, fatty acid esters (e.g., isopropyl myristate, methyl laurate, glycerol monooleate, and propylene glycol monooleate); N-methyl pyrrolidone; monovalent, saturated and unsaturated aliphatic cycloaliphatic and aromatic alcohols having 4 to 12 carbon atoms, such as hexanol, cyclohexane and the like; aliphatic cycloaliphatic and aromatic hydrocarbons having from 5 to 12 carbon atoms such as hexane, cyclohexane, isopropylbenzene and the like; cycloaliphatic and aromatic aldehydes and ketones having from 4 to 10 carbon atoms such as cyclohexanone; acetamide; N,N-di(lower) alkyl acetamides such as N,N-diethyl acetamide, N,N-dimethyl acetamide, N-(2-hydroxyethyl) acetamide, and the like; and other transporting agents such as aliphatic, cycloaliphatic and aromatic esters; N,N-di(lower) alkyl sulfoxides; essential oils; halogenated or nitrated aliphatic, cycloaliphatic and aromatic hydrocarbons; salicylate; polyalkylene glycol silicates; surfactants; mixtures thereof; and the like.

Alternatively, permeation of a therapeutic agent may be enhanced by removing hair from the application site by, e.g. clipping, shaving or use of a depilatory agent. Another permeation enhancer is heat. It is thought that heat enhancement can be induced by, among other things, using a radiating heat form, such as an infrared lamp, onto the application site after application of the transdermal patch.

Various methods may be used to place therapeutic agents or drugs onto the patch. For example, the therapeutic agent may be placed onto the patch by absorption, adsorption, chemical bond, and covalent bond.

For drug-in-matrix type patches, the therapeutic agent is dissolved or suspended in a polymer matrix film through which the active agent diffuses to the skin as disclosed in U.S. Pat. No. 4,839,174, 4,908,213, and 4,943,435.

The therapeutic agents or drugs suitable for use in this invention may be present in the reservoir, matrix, or microcapsules as explained supra. A carrier may be used together with the therapeutic agent when placed on the patch. The carrier material will typically be one of two types. One type bioerodes rather uniformly over time, so that the bioerosion of the carrier is also the primary mechanism for releasing the drug from a patch. The second type is a material which essentially remains intact during a substantial portion of the release period of the drug. The mechanism of release of the drug is by diffusion or other mechanism which does not require the carrier to be concurrently bioeroded. Many carrier materials may be suitable for various embodiments of the system of the present invention. These carrier materials may be natural products, such as keratin, triglycerides, fatty acids, lipids, latexes, as well as derivatives, salts of cellulose derivatives, alkaline or alkaline earth salts of cellulose acetate phthalate, ammonium salts of hydroxypropyl methyl cellulose phthalate, polysaccharide, synthetic polymers, such as, polyglycolic acid and derivatives of polyethylene glycol, polycaprolactone, polylactic acid, and copolymers thereof; materials such as starch, fatty alcohols, alginate polymers, albumin, calcium caseinate, calcium polypectate or gellan gum.

Adhesives for use with the drug-in-adhesive type patch are well known in the art and selection is readily accomplished by an ordinary practitioner. Three basic types commonly used are polyisobutylenes, silicones, and acrylics. Adhesives useful in the present invention can function under a wide range of conditions, such as, high and low humidity, bathing, sweating etc. Preferably the adhesive is a composition based on natural or synthetic rubber, polyacrylate, polyvinylacetate, polybutylacrylate, polymethylacrylate, polydimethylsiloxane, and hydrogels (e.g., high molecular weight polyvinylpyrrolidone and oligomeric polyethylene oxide). The most preferred is polyacrylate.

Therapeutic agents or drugs may also be glued onto the patch by means of a number of known synthetic, naturally-occurring or modified naturally-occurring substances which exhibit tackiness. The adhesive should be compatible with the material forming the carrier, as well as the drug. A variety of adhesives are suitable for the present invention, both for adhering a patch on the skin or mucosa, and for retaining therapeutic agent or drugs onto the patch. One adhesive is a hydrogel composed of gelatin and poly(L-glutamic acid) (PLGA). The hydrogel is formed by chemically cross linking gelatin and poly(L-glutamic acid). Another adhesive is fibrin glue. Suitable fibrin glue includes fibrinogen, thrombin, calcium chloride and factor VIII. Another family of adhesives is cyanoacrylates. Preferred cyanoacrylates include butyl-2-cyanoacrylate (Histoacryl), ethyl-2-cyanoacrylate, and octyl-2-cyanoacrylate. Gelatin-resorcinol formaldehyde-glutaraldehyde is another suitable adhesive. Others include carboxymethyl and hydroxypropyl methyl cellulose, and other cellulose derivatives; tragacanth, caraya, locust bean and other synthetic and natural gums such as algin, chitosan, starches, pectin, and naturally-occurring resins. In addition, many polymers having suitable adhesive properties can also be utilized, including without limitation: polyurethanes having amino groups, di- and tri-functional diols; polyvinyl acetates; polyamides; polyvinyl alcohols; polyvinyl pyrrolidone, polyacrylic acid; polystyrene; polylactides; polylactones; block co-polymers including polyesters, polyamides, and polyurethanes; and combinations and mixtures thereof.

In another embodiment, the therapeutic agent is applied onto the patch as a coating or layer. More than one coating of different therapeutic agents may be applied to the patch so that more than one therapeutic agent and/or carrier may be incorporated onto the patch. The placement of the different layers may be determined by the diffusion or elution rates of the therapeutic agent involved as well as the desired rate of delivering the therapeutic agent to the body tissue.

Selection of the appropriate dosage for transdermal delivery of therapeutic agent is an important consideration. The amount of active agent to be incorporated onto the patch to obtain the desired therapeutic effect will vary depending upon the desired dosage, the permeability of the rate controlling materials of the patch which are employed to the particular agent to be used, and the length of time the patch is to remain on the skin or body mucosa. Since this invention is designed to provide titratable dosage of drug. The dosage provided by the transdermal delivery system is proportional to the number of patch unit applied. The lower limit for dosages is determined by the fact that sufficient amounts of the drug must remain in each patch unit to maintain the minimum possible dosage. The dosages and dosing frequency will be determined by a trained medical professional. The concentration or loading of the therapeutic agent onto the therapeutic patch may be varied according to the therapeutic effects desired. Also, the loading, in terms of the ratio of therapeutic agent to carrier in the patch will depend upon the type of therapeutic agent and carrier used and the rate at which the therapeutic agent on the patch is released to the body tissue. Generally, the patch may contain 0.1–90% by weight or preferably 10–45% by weight of the therapeutic agent. Most preferably, 25–40% by weight of the therapeutic agent should be incorporated in the patch.

Concentrations of the drugs in the transdermal delivery system are virtually unlimited since delivery rate is controlled in various types of patches by a release limiting layer and an adhesive layer. However, the concentration must be at least great enough so that the drug will leave the vehicle once the protective cover layer is removed. One advantage of the present invention is that should the amount of drug/unit area/unit time be insufficient to render an appropriate dose of the drug, additional units of the transdermal patch of the present invention may be employed. However, it is more advantageous to utilize concentrations of drug sufficiently high so that patch size is kept down. Most advantageous are systems capable of delivering the drug in a therapeutically useful degree in an area reasonably related to the application site in view of medical, aesthetic, and patient convenience considerations. These limitations are well known to product designers in the art.

METHOD OF MAKING THE TRANSDERMAL DELIVERY SYSTEM

The present invention also relates to methods of making the transdermal delivery system. The method of the present invention generally involves forming a backing layer with a top surface and a bottom surface. The backing layer is divided into more than one unit at one or more lines of separation. A drug layer is disposed on the top surface of each unit of the backing layer, leaving a border on all sides of each of the unit of the backing layer. An adhesive means is used to attach the transdermal delivery system onto the skin or mucosa of the patient.

In one embodiment, the method further comprises disposing an adhesive layer on the drug layer and the border of the backing layer. A cover layer is then disposed on top of the adhesive layer. In one embodiment, the method of the present invention involves forming a backing layer with a top surface and a bottom surface. The backing layer is divided into more than one unit at one or more lines of separation. A drug-in-matrix layer is then disposed on the top surface of each unit of the backing layer, leaving a border on all sides of the backing layer. An adhesive layer is then disposed on the drug-in-matrix layer and the border of the backing layer. Finally, a cover layer is disposed on top of the adhesive layer.

The lines of separation formed distinct patch units on the backing layer. They also define each unit of the transdermal delivery system. The backing layer is made of materials as described supra. The backing layer has one or more lines of separation. A plurality of lines of separation are preferably parallel and/or perpendicular to each other. The lines of separation are also preferably spaced at regular intervals along the length and/or width of the backing. Preferably, the lines of separation are about 1 cm to 6 cm apart. The lines of separation may be in various forms as long as they allow for relatively clean separation of a desired number of units of the transdermal delivery system by the user as directed by a physician. The lines of separation may also be a weakness of the backing or a printed line of division so that a patient may tear along or use scissors to cut along the line. A preferred line of separation is a line of perforations. The weakness of the backing may be a thinning of the backing that is molded or formed in the backing. In some instances, it may be desirable to combine a line of weakness with perforations to ensure clean separation of the transdermal delivery system into a desired number of units for optimal dosage application. Other useful methods of constructing the lines of separation are disclosed in U.S. Pat. No. 5,496,605. It is important that the lines of separation allow easy division of the transdermal delivery system into desired number of units per application. Although the transdermal delivery system have been described as a transdermal delivery system having one or more lines of separation, those skilled in the art will understand that, alternatively, the present invention can also be characterized as a plurality of units of transdermal delivery patches connected to each other along the same line or lines of separation. Regardless of the characterization, the present invention provides a transdermal delivery system for and method of delivering therapeutic agent or drug of varying dosages using a single transdermal delivery system.

A drug-in-matrix layer is formed by dissolving or suspending a therapeutic agent in a polymer matrix through which the active agent diffuses to the skin. Methods of forming a drug-in-matrix layer are disclosed in U.S. Pat. No. 4,839,174, 4,840,796, 4,908,213, and 4,943,435. When a drug-in-matrix layer is disposed on the top surface of each unit of the backing layer, the drug-in-matrix layer is not coextensive with the entire unit of the backing layer. A border is left on all sides so that the backing layer is not entirely covered by the drug-in-matrix layer. This is to prevent the drug from seeping through the lines of separation. Various methods may be used to place a drug on the transdermal delivery system as discussed infra. An adhesive layer is then disposed on the drug-in-matrix layer, the adhesive layer also covers the border of the backing layer. The border is preferably uniform in width and can range from about 0 (zero) cm to about 2.0 cm. A cover layer is disposed on the adhesive layer so that each patch unit of the transdermal delivery system is protected separately. A notch is formed on the cover layer so as to facilitate separation of the cover layer from the adhesive layer when the transdermal patch is ready for use.

The present invention further provides a method of making the system of the present invention which involves forming a plurality of reservoir compartments within an enclosure defined by the raised wall directly on a backing layer. Each reservoir compartment is surrounded by a border having a surface. The plurality of the reservoirs are divided by one or more lines of separation on the border. A drug layer is disposed onto each unit of the reservoir compartment. An adhesive layer is then disposed on top of the drug layer and on the surface of the border. A cover layer is then disposed on the adhesive layer.

In this method of making a transdermal delivery system of the present invention, a plurality of reservoir compartments are formed on a backing layer. As mentioned earlier, each patch unit is surrounded by a border. The sidewalls of the reservoir compartment may be formed on the backing layer by raising the surrounding border or making a depression within the border. The height of the raised wall is determined by the quantity of therapeutic agent that is to be deposited in the reservoir compartment. However, it should be less than 5 mm so that it is comfortable for use by the patient. Each reservoir compartment is surrounded by a border. A line of separation is present on the border which allows the reservoir compartments to be separated into units.

The present invention also provides a method of making the system of the present invention which involves forming a backing layer with a top surface and a bottom surface. The backing layer is divided into more than one unit at one or more lines of separation. A drug-in-adhesive layer is disposed on the top surface of each unit of the backing layer, leaving a border on all sides of the backing layer. Then, a cover layer is disposed on top of the adhesive layer.

In this method of making a transdermal delivery system of the invention, the drug-in-adhesive layer is formed by mixing one or more drugs with an adhesive and dispose the composition on the top surface of each unit on the backing layer. A cover layer is disposed on the drug-in-adhesive layer so that each unit of the transdermal delivery system is protected separately.

The present invention further provides a method of making the system of the present invention which involves forming a backing layer with a top surface and a bottom surface. The backing layer is divided into more than one unit at one or more lines of separation. A drug-in-adhesive layer is disposed on the top surface of each unit of the backing layer, leaving a border on all sides of the backing layer. A semipermeable membrane is disposed on the drug-in-adhesive layer. The semi-permeable membrane is secured to the backing film so as to hold the drug-in-adhesive within the border. A second drug-in-adhesive layer is then disposed on the semi-permeable membrane. The border is then covered with an adhesive. Finally, a cover layer is disposed on top of each unit patch.

In this method of making a transdermal delivery system of the invention, the composition that is used to make a drug-in-adhesive layer is formed by mixing one or more drugs with an adhesive and dispose the composition on the top surface of each unit on the backing layer within the border.

METHOD OF USE FOR THE INVENTION

The method of the present invention can be used to deliver therapeutic agents or drugs systemically through the skin or mucosa of a patient.

The method comprises the steps of providing a transdermal delivery system of the invention. The user then separates the prescribed number of patch units from the transdermal delivery system along at least one line of separation along the border. The cover layer is then removed, exposing the adhesive layer and applying the prescribed number of the transdermal delivery patch units on the skin or mucosa. Alternatively, the user may remove the cover layer for a prescribed number of patch units from the transdermal delivery system and then separates the prescribed number of patch units from the transdermal delivery system. Under the direction of a physician, the user may increase or decrease the number of patch units used per application. In a preferred embodiment, the number of patch units used per application may be one, two, three, four or five.

The rate of transdermal delivery from the therapeutic patch is a function of skin permeability, and skin permeability has been shown to vary between anatomical sites depending on the thickness of the stratum corneum. For example, the permeability, in general, increases in order from planter foot arch, lateral ankle, palm, ventral forearm, dorsal forearm, back, chest, thigh, abdomen, scalp, axilla, forehead, and scrotum (Wester, R. C. and Maibach, H. I. (1989) Regional variation in Percutaneous Absorption: In *Percutaneous Absorption, Mechanism, Methodology, Drug Delivery*, $2^{nd}$ ed., Eds. R. L. Bronaugh and H. I. Maibach, Marcel Dekker, Inc., New York, pp. 111–119).

The transdermal delivery system of the invention may be applied directly to any area of the patient's skin, with the lower back, chest, upper arm, and buttocks being the areas of choice. In like manner, the patch can be applied to the mucosa of the mouth, for example, by application to the palate or the buccal mucosa, to obtain absorption of the drug by the oral mucosa. Similarly, where desired and accessible, the patch can be applied to other mucosa membranes.

In a preferred embodiment, the transdermal delivery system comprising a plurality of therapeutic patch units is stored in a resealable pouch. For each application, the transdermal delivery system is removed from the pouch and a prescribed number of patch units are removed from the pouch and applied on the skin or mucosa of a patient. The remaining patch units are placed in the resealable pouch.

In a preferred embodiment, the sustained delivery of the therapeutic agent will be for an extended period, longer than about three days and preferably, at least about one week. For treatment of cancer or other chronic conditions, it is preferred that the drug be delivered over a period up to about one month.

Whereas the invention has been shown and described in connection with specific embodiments hereof, many modifications, substitutions and additions may be made which are within the intended broad scope of the appended claims. Thus, it should be understood that the present invention encompasses the use of other methods and titratable dosage transdermal delivery systems for systemic delivery of adjustable dose of therapeutic agent to a patient.

Various references are cited herein, the disclosure of which are incorporated by reference in their entireties.

What is claimed:

1. A method of delivering a hormone through a patient's skin comprising:
   (a) providing a transdermal delivery system that comprises a plurality of patch units, wherein each patch unit comprises a backing layer having one or more borders, a drug layer comprising a hormone disposed on the backing layer, and an adhesive layer, wherein at least a portion of the adhesive layer is disposed on the borders of the backing layer; the plurality of patch units are connected to each other along one or more borders of the patch units; and each patch unit is defined by one or more lines of separation along the borders of the patch units;
   (b) separating at least one patch unit from the transdermal delivery system along at least one line of separation; and (c) applying at least one patch unit such that the drug layer makes contact with the skin.

2. The method of claim 1 wherein the patch units are applied on the skin of the planter foot arch, lateral ankle, palm, upper arm, ventral forearm, dorsal forearm, back, chest, thigh, abdomen, scalp, axilla, forehead, lower back, chest, buttocks or scrotum.

3. The method of claim 1 wherein a portion of the adhesive layar is disposed on the drug layer; and a cover layer is disposed on the adhesive layer.

4. The method of claim 1 wherein the hormone is selected from the group consisting of adrenocorticosteroids, 6-α-methylprednisolone, androgenic steroids, methyltestosterone, fluoxymesterone, progesterone, norethindrone, thyroxine, and insulin.

5. The method of claim 3 wherein said transdermal delivery system further comprises a release limiting layer disposed on the drug layer.

6. The method of claim 1 wherein the hormone is encapsulated by microcapsules.

7. The method of claim 1 wherein the drug layer comprises about 0.1–90% by weight of a hormone.

8. The method of claim 1 wherein the drug layer comprises about 10–45% by weight of a hormone.

9. The method of claim 1 wherein the drug layer comprises about 25–40% by weight of a hormone.

10. The method of claim 1 wherein the drug layer further comprises a softening agent selected from the group consisting of dodecanol, undecanol, octoanol, and esters of carboxylic acids.

11. The method of claim 1 wherein the drug layer further comprises a permeation enhancing agent.

12. The method of claim 3 wherein the cover layer comprises a notch so as to facilitate separation of the cover layer from the adhesive layer.

13. The method of claim 1 wherein the transdermal delivery system is stored in a resealable pouch.

14. The method of claim 1 wherein the lines of separation are parallel and/or perpendicular to each other.

15. The method of claim 1 wherein the lines of separation are lines of perforations.

16. The method of claim 1 wherein the lines of separation are spaced at regular intervals.

17. The method of claim 1 wherein the lines of separation are about 1 cm to 6 cm apart.

18. The method of claim 1 wherein 2 to 5 patch units are connected in series in the transdermal delivery system.

19. The method of claim 1 wherein 4 patch units are arranged in 2 rows and 2 columns in the transdermal delivery system.

20. The method of claim 1 wherein the drug layer is a reservoir layer.

21. The method of claim 1 wherein the drug layer is a drug-in-matrix layer.

22. The method of claim 1 wherein the drug layer is a drug-in-adhesive layer.

23. The method of claim 1 wherein two to five patch units are applied on the skin.

24. A method of adjusting the therapeutic dosage of hormone delivery through a patient's skin, the method comprising:
   (a) providing a transdermal delivery system that comprises a plurality of patch units, wherein each patch unit comprises a backing layer having one or more borders, a drug layer comprising a hormone disposed on the backing layer, and an adhesive layer, wherein at least a portion of the adhesive layer is disposed on the borders of the backing layer; the patch units are connected to each other along one or more borders of the patch units; and each patch unit is defined by one or more lines of separation along the borders of the patch units;
   (b) separating a first number of patch units from the transdermal delivery system along at least one line of separation;
   (c) applying the first number of patch units such that the drug layer makes contact with the skin;
   (d) thereafter, separating a second number of patch units from the delivery system along at least one line of separation, the second number of patch units being different than or the same as the first number of patch units; and
   (e) applying the second number of patch units such that the drug layer makes contact with the skin.

25. The method of claim 24 wherein one or more patch units from the first number of patch units are removed from the skin before applying the second number of patch units to the skin.

26. The method of claim 24 wherein one or more patch units from the first number of patch units remain on the skin before applying the second number of patch units to the skin.

27. The method of claim 24 wherein the hormone is selected from the group consisting of adrenocorticosteroids, 6-α-methylprednisolone, androgenic steroids, methyltestosterone, fluoxyrnesterone, progesterone, norethindrone, thyroxine, and insulin.

28. The method of claim 24 comprising increasing the dosage of hormone through the patient's skin, wherein the second number of patch units is greater than the first number of patch units.

29. The method of claim 24 comprising decreasing the dosage of hormone through the patient's skin, wherein the second number of patch units is less than the first number of patch units.

* * * * *